United States Patent [19]
Guth

[11] 4,292,978
[45] Oct. 6, 1981

[54] BREATH TEST MOUTHPIECE

[76] Inventor: Richard U. Guth, 439 N. 46th St., Harrisburg, Pa. 17111

[21] Appl. No.: 107,429

[22] Filed: Dec. 26, 1979

[51] Int. Cl.³ .................................................. A61B 10/00
[52] U.S. Cl. .................................... 128/730; 128/719; 55/440; 422/84
[58] Field of Search ............... 128/716, 717, 719, 730; 422/84, 85; 181/227, 268, 281; 55/440

[56] References Cited

U.S. PATENT DOCUMENTS

| | | | |
|---|---|---|---|
| 1,181,470 | 5/1916 | Massip | 55/440 |
| 1,186,067 | 6/1916 | Becker | 181/281 |
| 1,700,993 | 2/1929 | Bernet et al. | 181/268 |
| 3,612,039 | 10/1971 | Falk | 128/719 |
| 3,734,692 | 5/1973 | Lucker et al. | 128/719 |
| 3,853,477 | 12/1974 | Block et al. | 23/254 R |
| 3,880,591 | 4/1975 | Burroughs | 23/259 |
| 4,027,740 | 6/1977 | Martin | 181/281 |
| 4,167,987 | 9/1979 | Turner | 181/281 |
| 4,220,219 | 9/1980 | Flugger | 181/281 |

FOREIGN PATENT DOCUMENTS 1032177  6/1966  United Kingdom ............... 128/719

Primary Examiner—Kyle L. Howell
Attorney, Agent, or Firm—Thomas Hooker

[57] ABSTRACT

A breath-test mouthpiece of the type used to remove solids, saliva and water vapor from the breath of a subject being tested to determine a breath constituent, typically breath alcohol, including axially-aligned mouth and tube pipes with a hollow central collector having a lip-engaging edge to either side of the mouth pipe and an enlarged cross section multi-path interior baffle forcing the breath to flow along a serpentine-shaped path as it moves from the mouth pipe to the tube pipe.

23 Claims, 5 Drawing Figures

U.S. Patent  Oct. 6, 1981  4,292,978
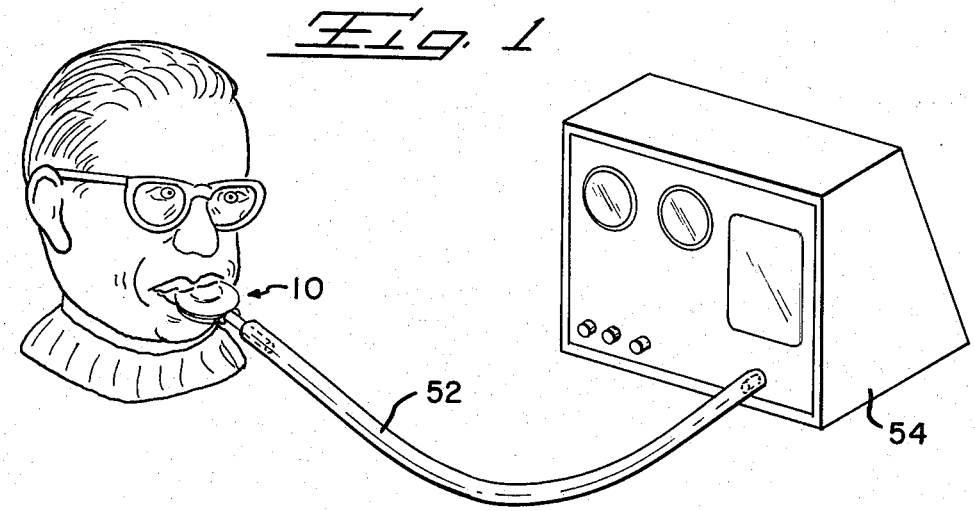
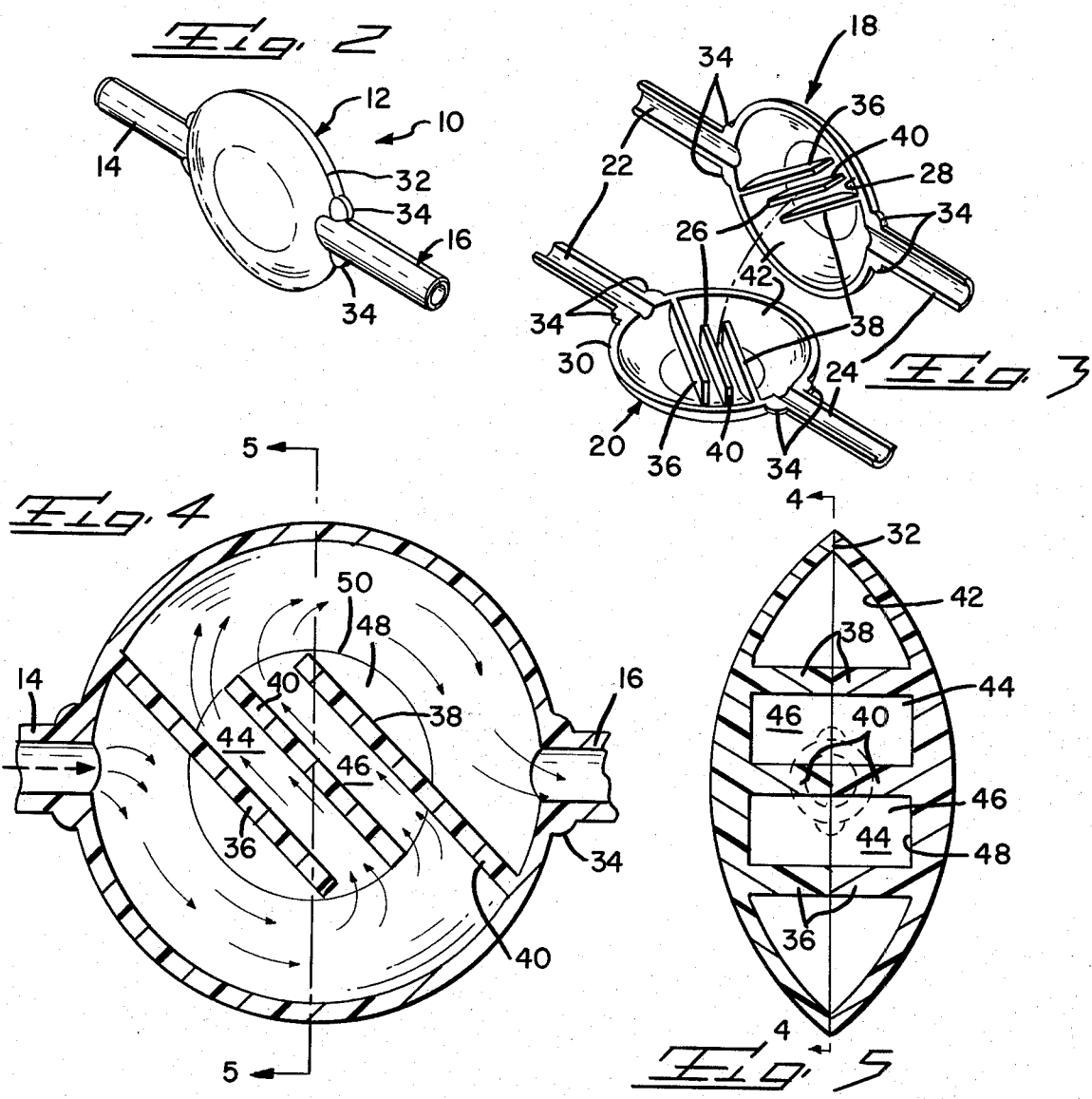

BREATH TEST MOUTHPIECE

This invention relates to mouthpieces of the type used when conducting breath tests, typically tests on drivers believed to be operating motor vehicles under the influence of alcohol. The instruments used in the test analyze the alcohol content of deep lung breath, which, in turn, gives an indication of the blood alcohol content of the subject.

The tests are conventionally conducted by attaching a sterile, disposable mouthpiece to the end of a flexible tube extending to the testing instrument. The mouthpiece includes a mouth pipe which is placed between the subject's lips, a collector portion intended to remove solid matter and saliva from the breath and a tube pipe inserted into the tube. A conventional mouthpiece is disclosed at FIG. 2 of U.S. Pat. No. 3,853,477. U.S. Pat. No. 3,880,591 discloses a cup-type breath-test mouthpiece different from the present invention.

The mouthpiece of the present invention is an improvement over conventional mouthpieces used for breath-test purposes. It includes a transparent plastic body having diametrically opposed mouth and tube pipes and a central collector having an interior cavity communicating with the pipes and baffle partitions defining a serpentine-shaped flow path for effectively collecting foreign matter, saliva and water vapor. The edge of the collector at the mouth pipe has an approximate 90° edge to facilitate forming a breath-tight seal with the lips of the subject. Additionally, fillets fill the corners between the intersections of the cylindrical breath pipe and the collector to further assure a tight seal with the lips.

The diametrically opposed breath and tube pipes assure that the officer administering the test can accurately determine the location of the tube pipe within the mouth of the subject. The tube pipe has sufficient length to form a straight and resilient seal with the instrument tube without bends which tend to loosen the seal at the end of the re-usable tube after a number of tests.

The flow path within the interior of the collector has a greater cross-sectional area than the interior of the mouth pipe. Solids flowed into the collector with the breath impinge on the interior sidewalls and are collected there while the gaseous breath flows through the serpentine shaped path and into the instruments. Saliva is also collected. Water vapor in the breath condenses on the interior walls of the collector. The transparent mouthpiece walls permit the operator to inspect the interior of the collector while the test is being conducted. Additionally, magnifying lenses are provided in the collector sidewalls to further facilitate inspection of the interior and also to magnify identifying indicia on the interior walls.

Other objects and features of the invention will become apparent as the description proceeds, especially when taken in conjunction with the accompanying drawing illustrating the invention, of which there is one sheet.

IN THE DRAWINGS

FIG. 1 illustrates use of the mouthpiece in administering a breath test;

FIG. 2 is a perspective view of the mouthpiece;

FIG. 3 is an exploded view showing two halves of the mouthpiece;

FIG. 4 is a sectional view of the mouthpiece, illustrating the flow of breath through the mouthpiece; and FIG. 5 is a sectional view taken along line 5—5 of FIG. 4.

Mouthpiece 10 is preferably made of molded transparent plastic material and includes a central hollow collector 12 with coaxial-like mouth and tube pipes 14 and 16 extending from opposite ends of the collector. The mouthpiece is formed from two half members 18 and 20 with each half member including semi-cylindrical mouth pipe and tube pipe portions 22 and 24 and a central outwardly domed collector portion 26. Planar mounting surfaces 28 and 30 extend along the length of the two half members 18 and 20 and around the collector portions. These surfaces are secured together, conventionally by ultrasonic welding, to form the unitary mouthpiece 10 with an edge seam 32 extending along the length of each side thereof. The half members include reinforcing fillets 34 at the junctions between the tube and the mouth pipes and the collector portions. The fillets strengthen the connection between these members and also, by providing an increased area per surfaces 28 and 30, increase the strength of the bond between the two half members.

Each half member 18 and 20 includes three parallel partitions 36, 38 and 40 upstanding from the interior surface 42 of the collector portion with the tops of the partitions lying on the plane of surfaces 28 and 30. One end of partition 36 joins the interior surface 42 adjacent and to one side of the mouth pipe portion 22 and angles across the interior of the collector portion 26 at 45° to the axis of the pipes 14 and 16 to a free end spaced from the interior surface 42. Partition 38 extends upwardly from the surface 42 with one end joining the surface adjacent the tube pipe portion 24 and angling therefrom across the collector portion 26 at an angle of 45° to the longitudinal axis of the pipes to a free end spaced from surface 42. Partition 40 has free ends spaced from adjacent surface 42 and is located between partitions 36 and 38 with free ends adjacent the free ends of the other partitions. As illustrated in FIG. 3, the partitions of the two half members 18 and 20 are angled in opposite directions with respect to the longitudinal axis of the pipes so that when the half members are placed one on top of the other and bonded together the top walls of the partitions are joined to strengthen the bond between the members.

The partitions also define the flow path for breath blown through the collector from the mouth pipe 14 to tube pipe 16. This path is serpentine in shape with a pair of 180° bends located before and after the breath passes through the two parallel passages 44 and 46 defined by the partitions. Additionally, the breath is deflected 45° by the wall formed by partitions 36 upon entry into the collector. The serpentine flow path, including each passage 44, 46, has a greater cross-sectional area than the cross-sectional area of the mouth or tube pipes.

The mouthpiece 10 is symmetrical to either side of the section line shown in FIG. 4 so that breath may be blown from pipe 14 to pipe 16 or vice versa. The officer conducting the breath test need not be concerned about proper orientation of the mouthpiece when he attaches it to the testing instrument.

As illustrated in FIGS. 4 and 5, surface 42 includes a central circular flat area 48 defined by perimeter 50. The thickness of the domed transparent collector wall at surface 48 varies to form a magnifying glass, thereby enabling inspection of the interior of the mouthpiece.

The magnifying glass also magnifies indentifying indicia such as the name of the manufacturer located on the interior surface 48.

In order to conduct a breath test, the supervising officer inserts the tube pipe 16 of a clean, sterile mouthpiece 10 into the free end of a flexible breath tube 52, the other end of which is attached to a testing instrument 54 capable of analyzing breath vapor. The subject is then instructed to place the mouth pipe 14 within his mouth so that his lips seat against the exterior surface of the collector adjacent the mouth pipe. The interior angle between the collector portions at edge seam 32 is approximately 90° so that the mouthpiece is easily held between the subject's lips with the seam extending across the lips and conforming with the closure of the lips see FIG. 1. In this way, a tight seal is easily and naturally formed between the lips and mouthpiece so that exhaled breath flows through the mouthpiece and tube to the instrument. The fillets 34 adjacent mouth pipe 14 extend outwardly from the mouth pipe and collector to fill the recess at the seam and aid in forming a seal between the mouthpiece and the lips of the subject.

Mouth pipe 14 is located on an extension of a diameter of the collector so that the mouthpiece fits symmetrically within the mouth of the subject. This is important since it assures the mouthpiece can be easily held in place by a subject who may be inebriated. The mouth pipe 14 is sufficiently long that when the subject's lips are seen to abut the collector 12, the officer conducting the test is assured that the end of the mouthpiece is within the mouth cavity a distance making it difficult for the subject to close the mouth pipe with his lips. The tube pipe 16 likewise is sufficiently long to form a tight, secure seal with tube 52 so that all the breath blown into the mouthpiece is flowed to instrument 54 and accidental venting is eliminated.

The breath blown by the subject into mouth pipe 14 follows a serpentine path as shown in FIG. 4. Breath leaving pipe 14 enters the expanded area interior of collector 12 and is deflected through an angle 45° by the wall formed by partitions 36. The breath is then deflected by surface 42 and the wall formed by partitions 38 through an angle of approximately 180° and flows through the passages 44 and 46 to an approximate 180° bend leading to an acute-angle bend at the inlet of the tube pipe 16. These changes in direction deposit foreign matter in the collector.

Foreign matter entrained with the breath, such as food particles, tobacco and the like, is removed from the breath so that the gaseous content of the breath only is received by instrument 54. Food and other solid particle are first collected on partition 36. Solid particles also collect at the first 180° bend of the breath before it flows into passages 44 and 46. The use of parallel flow paths between the partitions provides a continuous breath path to the instrument even if one passage should become clogged by solids. Foreign matter carried through the passages 44 and 46 is deposited at the following 180° bend.

Liquid saliva carried with the exhaled breath will be trapped within the mouthpiece, primarily below the first 180° bend of the breath path. The cross-sectional area of the flow path through the mouthpiece, even within each passage, 44 or 46, is greater than the interior cross-sectional area of the tubes 14 and 16. This increased surface area within the mouthpiece effectively condenses the water vapor in the breath since the mouthpiece is usually cooler than body temperature. The water vapor clouds or whitens the interior surfaces of the transparent mouthpiece and is easily observed by the person administering the test in order to assure that the subject is exhaling properly into the testing apparatus. The transparent mouthpiece also enables the operator to determine whether particulate matter and solids are collecting sufficiently to either clog the mouthpiece or impair the validity of the test.

Prior mouthpieces of the type shown in FIG. 2 of U.S. Pat. No. 3,853,477 feature short and laterally offset mouth and tube pipes. The collector portion of these mouthpieces have flat peripheral sidewalls extending across nearly the entire width of the mouthpiece. As a result, it is easy for the subject to only partially close his lips around the pipe and mouthpiece thereby allowing exhaled breath to be vented through the lips rather than blown through the mouthpiece and to the testing instrument. This undesired venting could result in an improperly low reading in the case of alcohol breath testing. Because the tube pipe of the mouthpiece is diametrically offset, forcing of the tube onto the pipe tends to twist and distort the tube because it first engages the collector on one side of the tube only. This tends to loosen the tube on the pipe and to reduce the effectiveness of the seal. In use, the subject tends to hold the mouthpiece so that the mouth pipe is located centrally between his lips and extends angularly into his mouth. This means that the breath tube extending to the instrument is bent at the off-center tube pipe. With continued use of the breath tube in taking successive tests the end of the tube pipe tends to be enlarged thereby reducing the effectiveness of the seal and increasing the chance of leakage. All of these factors are very important when it is understood that under the law a testing officer may only be entitled to conduct a single breath test of the subject in order to determine blood alcohol content. The accuracy of the breath test may be impaired due to breath leakage or lack of cooperation by the subject in partially blocking the flow of breath through the mouthpiece. The improved shape and baffle of the present mouthpiece reduces the difficulties experienced by the officer administering the test, particularly where the subject has difficulty blowing.

While mouthpiece 10 is primarily intended to be used in breath testing of persons suspected of driving under the influence of alcohol, it obviously may be used to remove solids, saliva and water vapor from breath in connection with other types of breath testing or analysis. It is understood that the disclosed preferred embodiment of my mouthpiece is capable of modification, and I therefore do not wish to be limited to the precise details as set forth, but desire to avail myself of such changes and alterations as fall within the purview of the following claims.

What I claim my invention is:

1. A handheld mouthpiece of the type used in conducting a breath test including a hollow central collector, a mouth pipe and a tube pipe extending from the collector and communicating with the interior of the collector, a breath baffle within the interor of the collector for changing the direction of the breath blown through the mouthpiece and trapping solids and liquid entrained with the breath, wherein the improvement comprises said pipes being located on opposite sides of the collector, the collector adjacent the mouth pipe including a first wall, a second wall and an edge joining the two walls, the mouth pipe extending outwardly of the collector at the edge between the walls, and the first and second walls joining the edge at an interior angle of about 90°, whereby the mouth pipe may be held within the mouth of a subject taking a breath test with the lips of the subject seated on the walls of the collector to form a breath-tight seal on the mouthpiece.

2. A mouthpiece as in claim 1 wherein said tubes are axially aligned, the baffle includes at least three spaced partitions extending across the interior of the collector so as to define a pair of flow paths therebetween, the inlet ends of said flow paths being located further away from the mouth pipe than the outlet ends of said flow paths so that the breath is channeled by the partitions to flow through a generally serpentine-shaped path between said pipes.

3. The mouthpiece as in claim 1 including fillets at the junctions between said edge and the inlet pipe so as to improve the seal with the lips of the subject.

4. A mouthpiece as in claim 3 wherein said walls include a magnifying lens.

5. A mouthpiece as in claim 4 wherein said lens overlies said baffle.

6. A mouthpiece as in claim 1 wherein said baffle includes an impinging partition located opposite said mouth pipe and oriented at an angle thereto to deflect breath to one side of the collector and a second partition spaced from and cooperative with said first partition position to deflect the breath about an approximate 180° angle, said second partition extending across the axis whereby said partitions cooperate to deflect the breath about a sinuous path between the inlet and outlet pipes.

7. A mouthpiece as in claim 6 including a third partition located between said tube partitions to define a pair of flow paths, each of said flow paths having a cross-section area greater than the cross-section area of said mouth pipe.

8. A mouthpiece as in claim 1 wherein said edge extends around the collector between said pipes and is generally circular and the collector to either side of the edge is domed.

9. A handheld mouthpiece of the type used in conducting a breath test including a hollow collector, a mouth pipe leading into the interior of the collector and a tube pipe leading away from the interior of the collector, a breath baffle within the interior of the collector including first, second and third spaced and generally parallel partitions extending across the interior of said collector, the first partition joining one interior wall of the collector and extending therefrom at an angle past the inlet pipe to a free end spaced from the opposite interior wall of the collector, a second partition joining the opposite interior wall of the collector adjacent the outlet pipe and extending therefrom at an angle past the outlet pipe to a free end spaced from said one interior wall of the collector, and a third partition between said first and second partitions dividing the space therebetween into a pair of flow paths.

10. A mouthpiece as in claim 9 wherein said mouth pipe and tube pipe are axially aligned on opposite sides of said collector.

11. The mouthpiece as in claim 10 where said collector includes a magnifying lens.

12. A mouthpiece as in claim 9 wherein the collector to either side of the mouth pipe defines an interior angle of approximately 90°.

13. A mouthpiece as in claim 12 including fillets located in the intersections of said angle and the mouth pipe.

14. A mouthpiece as in claim 9 wherein said collector is generally circular and said mouth pipe and tube pipe are coaxial with a common diameter, said partitions all intersecting said diameter.

15. A mouthpiece as in claim 9 wherein each said flow path has a cross-sectional area greater than the cross-sectional area of said mouth pipe.

16. A handheld mouthpiece of the type used in conducting a breath test including a hollow central collector, a first pipe extending away from the collector, a breath baffle within the interior of the collector for changing the direction of breath blown through the collector and collecting solids and liquids entrained with the breath, a breath outlet spaced from the first pipe, the first pipe, collector and outlet defining a breath path through the mouthpipe, wherein the improvement comprises the collector adjacent the first pipe including a first wall, a second wall and an edge joining the two walls, the first pipe extending outwardly of the collector at the edge between the walls, said first and second walls joining the edge at an interior angle, the edge lying generally in a plane extending through the first pipe whereby the first pipe and edge may be held within the mouth of the subject taking the breath test with lips forming a breath-tight seal on the mouthpiece.

17. A mouthpiece as in claim 16 wherein the interior angle is about 90°.

18. A mouthpiece as in claim 16 including an axis extending across the collector, the breath outlet comprising a second pipe, said pipes being located on said axis on opposite sides of the collector.

19. A mouthpiece as in claim 18 wherein the edge of the collector to either side of the second pipe comprises the vertex of the interior angle whereby either pipe may be held within the mouth of the subject taking the breath test with the subject's lips forming a breath-tight seal on the mouthpiece.

20. A mouthpiece as in claim 19 wherein the edges adjacent the pipes are coplanar.

21. A mouthpiece as in claim 20 consisting of a pair of like parts joined on a plane of symmetry extending through the center of the collector and perpendicular to both the axis and the plane defined by the edges.

22. A mouthpiece as in claim 20 wherein said edge extends around the collector between the first pipe and the second pipe and is generally circular.

23. A mouthpiece as in claim 16 wherein the collector includes a magnifying lens for viewing the breath baffle.

* * * * *